(12) United States Patent
Reimer et al.

(10) Patent No.: US 7,585,618 B2
(45) Date of Patent: Sep. 8, 2009

(54) TREATMENT OF DIABETES WITH MILK PROTEIN HYDROLYSATE

(75) Inventors: Raylene Reimer, Epalinges (CH); Christian Darimont-Nicolau, Lausanne (CH); Katherine Mace, Lutry (CH); Sandrine Gremlich, La Tour-de-Trême (CH); Jean-Richard Neeser, Savigny (CH)

(73) Assignee: Nestec S.A., Vevey (CH)

( * ) Notice: Subject to any disclaimer, the term of this patent is extended or adjusted under 35 U.S.C. 154(b) by 204 days.

(21) Appl. No.: 11/110,093

(22) Filed: Apr. 19, 2005

(65) Prior Publication Data

US 2005/0186558 A1 Aug. 25, 2005

Related U.S. Application Data

(60) Division of application No. 10/153,531, filed on May 21, 2002, which is a continuation of application No. PCT/EP00/10716, filed on Oct. 27, 2000.

(30) Foreign Application Priority Data

Nov. 22, 1999 (GB) ................. 9927603.2

(51) Int. Cl.
*C12Q 1/00* (2006.01)
*C12Q 1/02* (2006.01)
*C12N 5/08* (2006.01)

(52) U.S. Cl. .............. 435/4; 435/29; 435/366; 435/948

(58) Field of Classification Search ........... 435/4
See application file for complete search history.

(56) References Cited

U.S. PATENT DOCUMENTS 4,992,420 A 2/1991 Neeser
4,994,441 A 2/1991 Neeser

FOREIGN PATENT DOCUMENTS

EP 0629 350 A1 12/1994
WO WO 98/31239 7/1998

OTHER PUBLICATIONS

Hansen et al. Pediatric Research, (1996) vol. 40, No. 4, pp. 547-552; abstract.*
De Bruine, Adriaan P et al., "NCI-H716 cells as a model for endocrine differentiation in colorectal cancer", Virchows Archiv B Call Pathology Including Molecular Pathology, vol. 62, No. 5, 1992, pp. 311-320, XP001002588.
Drucker, Daniel J., et al., "Activation of proglucagon gene transcription by protein kinase-A in a novel mouse enteroendoctrine cell line", Molecular Endocrinology, vol. 8, No. 12, 1994 pp. 1646-1655, XP002169100.
Knapper et al. Hormone and Metabolic Research, (1995), vol. 27, No. 1, pp. 485-490.

\* cited by examiner

*Primary Examiner*—Vera Afremova
(74) *Attorney, Agent, or Firm*—Gary M. Lobel

(57) ABSTRACT

A milk protein hydrolysate which is preferably caseinoglycomacropeptide and/or a whey protein in a bioavailable form is used for the manufacture of a composition for the treatment or prevention of diabetes or syndrome X. The invention also relates to a method of treatment or prevention of diabetes or syndrome X utilizing such compositions, a method for assessing proglucagon gene expression and GLP-1 release by a cell line derived from an adenocarcinoma of human caecum.

2 Claims, 4 Drawing Sheets

TREATMENT OF DIABETES WITH MILK PROTEIN HYDROLYSATE

CROSS-REFERENCE TO RELATED APPLICATIONS

This application is a divisional of U.S. patent application Ser. No. 10/153,531 filed May 21, 2002, which is a continuation of the U.S. national stage designation of International application PCT/EP00/10716, filed Oct. 27, 2000, the entire content of which is expressly incorporated herein by reference.

FIELD OF THE INVENTION

The present invention relates to use of milk protein hydrolysates in the manufacture of a medicament for the treatment or prevention of diabetes or syndrome X and a to a method of treatment of diabetes or syndrome X which comprises administering an effective amount of a composition comprising such milk protein hydrolysates. The present invention also relates to the use of sweet whey or acid whey proteins or protein hydrolysates in the manufacture of a medicament for the treatment or prevention of diabetes or syndrome X and to a method of treatment or prevention of diabetes or syndrome X that comprises administering an effective amount of such compositions. Furthermore, the present invention relates to the use of caseino-glycomacropeptide ("CGMP") in the manufacture of a medicament for the treatment or prevention of diabetes or syndrome X and to a method of treatment or prevention of diabetes or syndrome X that comprises administering an effective amount of such compositions. In addition, the present invention relates to the use of NCI-H716 cells, obtained from a cell line derived from a poorly differentiated adenocarcinoma of human caecum (de Bruine et al., Virchows Archiv B Cell Pathol 62:311-320 (1992)), as a model to measure proglucagon gene expression and GLP-1 secretion.

BACKGROUND OF THE INVENTION

B. Chabance et al. (Biochimie 80, 155-165, 1998) have shown that after eating, many peptides derived from α-, β- or κ-caseins, including CGMP, can be detected in stomach and blood, thus indicating that these peptides can cross the intestinal barrier.

Diabetes mellitus is a metabolic disorder characterized by the failure of body tissues to store carbohydrates at the normal rate. Resistance to the action of insulin is the most important factor to type II diabetes. When this resistance exceeds the capacity of the beta cells to produce insulin, a person becomes diabetic. During the last 70 years people suffering from diabetes have been greatly aided by receiving controlled amounts of insulin.

Historically, insulin has been administered by injection to combat diabetes. Administering an injection requires expertise, and compared to oral administration, injecting a medicament is not as safe, convenient or acceptable to the patient. In light of these concerns, it is clear that there is a need for new nutritional or therapeutic products that may be administered orally.

Proglucagon, synthesized by L-cells found in the distal ileum and colon, is known to be post-translationally processed into peptides including glucagon-like peptide-1 (GLP-1), a potent insulin secretagogue. In addition to potentiating glucose-induced insulin secretion, GLP-1 is known to stimulate proinsulin gene expression and proinsulin biosynthesis. Other actions of GLP-1 include the inhibition of glucagon secretion and gastric motility. GLP-1 can bind in the brain, promoting satiety and suppressing food intake. Increasing insulin secretion is a key goal in the treatment of type II diabetes and stimulation of endogenous release of GLP-1 is a potential/prospective alternative to intravenous administration.

Improving glucose control in diabetes can provide the advantage of reducing the associated risks of hyperglycemia, including blindness, limb amputations, kidney failure and cardiovascular disorders.

A number of in vitro cell models of animal origin have been developed to study the regulation of GLP-1 secretion including a fetal rat intestinal cell culture, an isolated canine L cell, a secretin tumor cell (STC-1) cell line, and the GLUTag enteroendocrine cell line. While these models have provided useful information regarding the factors which regulate GLP-1 secretion and proglucagon expression, they suffer from the problem that they do not necessarily represent the same regulators and mechanisms which are active and occur in human L cells.

The present invention addresses the problems set out above.

SUMMARY OF THE INVENTION

Remarkably, it has now been found that a milk protein hydrolysate can induce the release of GLP-1 and can be used to improve glucose homeostasis in vivo.

In fact, in contrast to known studies, NCI-H716 cells have now been employed, obtained from a cell line derived from a poorly differentiated adenocarcinoma of human caecum (de Bruine et al, Virchows Archiv B Cell Pathol 62:311-320 (1992)). Surprisingly, the NCI-H716 cell line has now been found to be a good model for the first study of potential secretagogues that regulate human GLP-1 secretion in vitro. Up to now, NCI-H716 cell line was not known to be suitable for this purpose. Nor was it previously known that any human cell line would be capable of releasing GLP-1. So far, only cell lines derived from animals were available to serve as in vitro models to study proglucagon gene expression and GLP-1 secretion. This property of the present cell line will enable much simplified research on GLP-1 release.

Furthermore, the results obtained by the use of a human cell line to conduct studies on the production or function of GLP-1 will be much more relevant than results derived from other animal models. In short, the NCI-H716 cell line derived from a poorly differentiated adenocarcinoma of human caecum is likely to become a key tool for studying proglucagon gene expression and GLP-1 secretion in humans. This cell line is deposited and available at the ATCC (American Type Culture Collection) under the ATCC Number CCL-251. The depositor is A. F. Gazdar and the tissue of origin is the caecum: it is derived from a colorectal adenocarcinoma.

Consequently, in a first aspect the present invention relates to the use of a milk protein hydrolysate that is capable of inducing release of GLP-1 in the manufacture of a composition for the treatment or prevention of diabetes or syndrome X.

In a second aspect, the invention provides a method of treatment or prevention of diabetes or syndrome X which comprises administering to a person in need of such treatment an effective amount of a milk protein hydrolysate which is capable of inducing release of GLP-1 in an amount effective to treat or prevent diabetes or syndrome X.

In a third aspect, the present invention provides a model for the study of proglucagon gene expression and GLP-1 production by humans which includes cells obtained from a cell line derived from an adenocarcinoma of human caecum.

In a further aspect, the invention relates to a method for assessing proglucagon expression and GLP-1 release in humans by utilizing a cell line derived from an adenocarcinoma of human caecum.

Yet another aspect of the invention relates to the use of a cell line derived from an adenocarcinoma of human caecum to assess proglucagon gene expression and GLP-1 release in vitro.

An advantage of the present invention is that it provides a composition that can be administered orally. This is both safer and more convenient for the patient than conventional treatment by injection of insulin.

Another advantage of the present invention is the reduced risk of hypoglycemic reactions. Conventional injection of insulin carries with it the undesirable side effect of hypoglycemic reactions. The use of oral hypoglycemic agents to augment insulin secretion can also result in hypoglycemic reactions. Once the plasma glucose levels reach fasting values, GLP-1 no longer stimulates insulin release. The advantage of enhancing insulin release via GLP-1 secretion is that the action of GLP-1 is glucose dependent and therefore eliminates the risk of hypoglycemia, i.e., the release of insulin is very fine-tuned with respect to the blood glucose levels that are actually present.

Yet another advantage is that GLP-1 remains active in persons with diabetes whereas incretin hormone, glucose dependent insulinotropic peptide (GIP) loses effectiveness in treating diabetes in such subjects.

Still another advantage of the present invention is that it provides metabolic benefits in addition to the augmentation of insulin release. Conventional treatments raise insulin levels, but the present invention in addition increases insulin mRNA, increases beta-cell sensitivity, and lowers glucagon levels.

Another advantage of the present invention is that it provides a composition that can regulate appetite and reduce food intake. This action is beneficial in controlling diabetes and syndrome X.

BRIEF DESCRIPTION OF THE DRAWINGS

Additional features and advantages of the present invention are described in, and will be apparent from, the description of the presently preferred embodiments that are set out below with reference to the drawing figures in which.

DETAILED DESCRIPTION OF THE PREFERRED EMBODIMENTS

Figure 1:
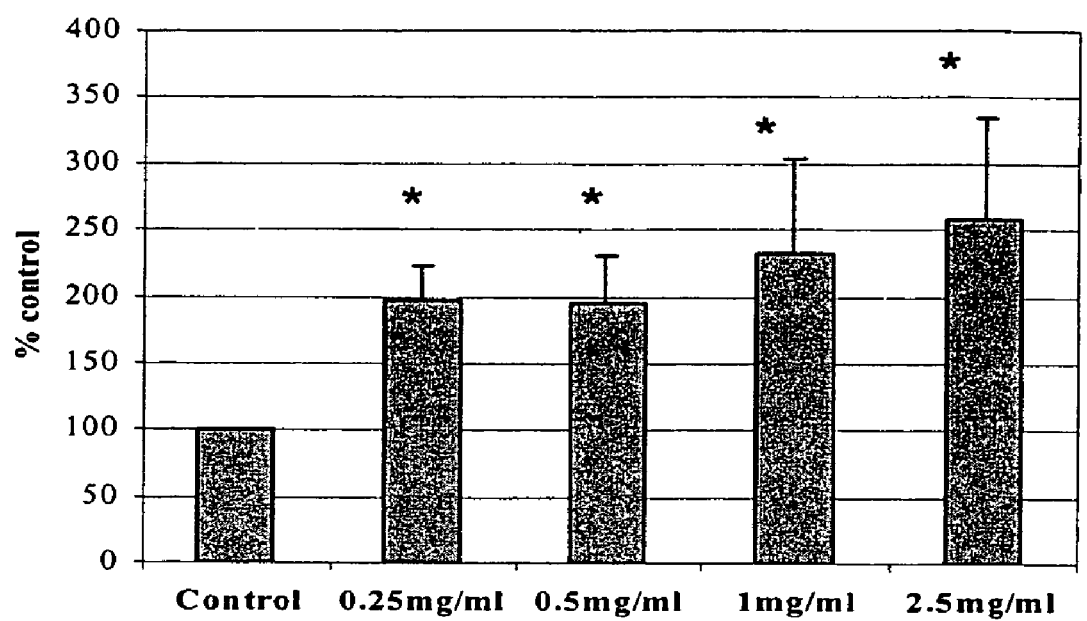
FIG. 1 shows secretion of GLP-1 by NCI-H716 cells in response to incubation for 2 h with different doses of CGMP-Ca form.

Within the context of this specification the word "comprises" is taken to mean "includes, among other things". It is not intended to be construed as "consists of" or "only".

Within the context of this specification the term "milk protein hydrolysate" is taken to mean milk proteins that have been subjected to any type of hydrolysis. Thus, such milk protein hydrolysate may even include intact proteins that escaped hydrolysis and also any fractions of proteins obtained by the treatment of the hydrolysis.

Within the context of this specification the terms "sweet whey" and "acid whey" are also considered to be possible milk protein hydrolysates, because these materials are the product of enzymatic or acid hydrolysis of milk proteins. Whey, however, as is well known in the art, can also comprise intact proteins as well as different fractions of hydrolysed proteins.

CGMP is a milk protein hydrolysate. It is a sialylated macropeptide that is formed by the action of rennet or pepsin on kappa-casein from the milk of mammals. An alternative name for CGMP is k-caseinoglyco-peptide. CGMP-Ca and CGMP-Na are used as abbreviations for the calcium salt and sodium salt, respectively, of CGMP.

The preferred milk protein hydrolysates that are capable of inducing release of GLP-1 comprise CGMP, or a mimetic, a homologue or a fragment thereof that retains the activity of CGMP. A particularly preferred embodiment of the milk protein hydrolysate is the calcium or sodium salts of CGMP.

Advantageously, the composition includes one or more of a source of carbohydrate, a source of fat and a source of protein. The preferred compositions comprise from about 15 to about 25% protein, from about 10 to about 30% fat, and from about 40 to about 60% carbohydrate. Preferably, at least a portion of the protein is provided as protein from sweet whey or acid whey, while more preferably, at least a portion of the protein is provided as CGMP. Other preferred milk protein hydrolysates which are capable of inducing release of GLP-1 comprise proteins that are present in sweet whey or acid whey.

One or more of these compositions are advantageously incorporated into a food formula. When this is done, the composition comprises from about 1 to about 50 grams, preferably from 5 to about 25 grams and more preferably from 5 to about 10 grams CGMP per 100 g of food formula.

The composition may be administered to provide sufficient whey protein, CGMP or mixtures thereof to improve glucose metabolism in humans or companion animals by increasing plasma GLP-1 levels and controlling glycemic response. The exact amount can be determined without difficulty by administering different amounts until the correct effect is seen. The dose of whey proteins and/or CGMP is typically from about 1 to about 50 grams per day, preferably from 9 to about 18 grams per day and more preferably from 3 to about 6 grams consumed at three times throughout a day.

It is well known in the art how a milk or whey protein can be obtained. In general, skimmed milk is treated with enzymes or acid in order to finally separate sweet or acid whey, respectively, which is thus deprived from the clotted casein. The sweet or acid whey then comprises whet protein hydrolysates and also minor proteins, which remain intact. Thus, sweet or acid whey can be obtained, e.g., as a side product from the production of cheese. Although it is not necessary to additionally process whey for use in the present invention, it is obvious to the skilled artisan that further processing is possible. For example, sweet and acid fluid whey can be condensed, dried, fermented, delactosed, demineralized, and deproteinated.

It is also possible to use whey concentrate or whey powder. The latter is especially convenient for addition to any chosen food product to produce the desired effect. It is also clear to the skilled artisan that protein hydrolysates present in sweet or acid whey can be further hydrolysed, e.g., to prepare a hypoallergenic whey protein hydrolysate. According to U.S. Pat. No. 5,039,532, whey protein material may be subjected to a second hydrolysis with a proteolytic enzyme in order to hydrolyse the minor proteins remaining intact after the first hydrolysis. Such a hydrolysate may then be used as a liquid or may be dried to a powder for incorporation into numerous food products.

CGMP may be obtained by an ion-exchange treatment of a liquid lactic raw material containing CGMP. Suitable starting materials of lactic origin may include for example, any of the following:

the product of the hydrolysis with rennet of a native casein obtained by acidic precipitation of skimmed milk with a mineral acid or acidifying ferments, optionally with addition of calcium ions, the hydrolysis product of a caseinate with rennet, a sweet whey obtained after separation of casein coagulated with rennet, a sweet whey or such a whey demineralized, for example, by electrodialysis and/or ion exchange and/or reverse osmosis, a concentrate of sweet whey, a concentrate of whey proteins obtained by ultrafiltration and diafiltration of sweet whey.

mother liquors of the crystallization of lactose from a sweet whey, or a permeate of ultrafiltration of a sweet whey.

A preferable method of obtaining CGMP is described, for example, in WO98/53702, and includes the decationization of the liquid raw material, such that the pH is at a value of 1 to 4.5, bringing the liquid into contact with a weak anionic resin of hydrophobic matrix, predominantly in alkaline form up to a stabilized pH, and then separating the resin from the liquid product, followed by desorption of CGMP from the resin.

A preferred embodiment of this composition comprises a milk protein hydrolysate. It has been shown that skimmed milk results in CGP levels of 1.1 µg/ml in human plasma. After yogurt ingestion, 2.8 µg/ml of CGP can be detected in the blood.

As noted above, the most preferred milk protein hydrolysates comprise CGMP.

The composition can also contain a source of protein and at least protein hydrolysates from sweet whet or acid whey and/or CGMP. Dietary protein is preferably used as a source of protein. The dietary proteins may be any suitable dietary protein; for example animal protein (such as milk protein, meat protein or egg protein); vegetable protein (such as soy protein, wheat protein, rice protein, or pea protein); a mixture of free amino acids; or a combination thereof. Milk proteins such as casein, whey protein or soy proteins are particularly preferred.

The composition may also contain a source of carbohydrate and/or a source of fat. In a preferred embodiment of the composition, the fat source provides about 5% to about 55% of the energy of the nutritional formula; for example about 20% to about 50% of the energy. The lipids making up the fat source may be any suitable fat or fat mixture. Vegetable fat is particularly suitable; for example soy oil, palm oil, coconut oil, safflower oil, sunflower oil, corn oil, canola oil, along with lecithins or the like, ether used alone or in mixtures thereof. Animal fat such as milk fat may also be added if desired.

It is also preferable to include in the composition a source of carbohydrate. When used, the carbohydrate provides about 40% to about 80% of the energy of the nutritional composition. Any suitable carbohydrate may be used, for example sucrose, lactose, glucose, fructose, corn syrup solids, and maltodextrins, or mixtures thereof.

It is also desirable for the composition to include dietary fibers. When used, these can provide up to about 5% of the energy of the nutritional formula. The dietary fiber may be from any suitable origin, including for example soy, pea, oat, pectin, guar gum, gum arabic, fructooligosaccharide, or mixtures thereof.

In addition, one or more suitable vitamins and/or minerals may be included in the composition in amounts that can meet appropriate guidelines.

One or more food grade emulsifiers may be incorporated into the nutritional formula if desired, such as, e.g., diacetyl tartaric acid esters of mono- and di-glycerides, lecithin and mono- and di-glycerides. Similarly suitable salts and stabilizers may also be included.

A preferred embodiment of the composition is enterally administrable; e.g., in the form of a powder, a liquid concentrate, or a ready-to-drink beverage. If it is desired to produce a powdered nutritional formula, the homogenized mixture can be transferred to a suitable drying apparatus such as a spray drier or freeze drier and then be converted to powder.

In a further embodiment, a typical food product may be enriched with whey protein and/or CGMP to provide inventive compositions. For example, a fermented milk, a yogurt, a fresh cheese, a renneted milk, a confectionery bar, breakfast cereal flakes or bars, drinks, milk powders, soy-based products, non-milk fermented products or nutritional supplements for clinical nutrition. In these products, the amount of whey protein and/or CGMP that is added is at least about 0.01% by weight.

In an alternative embodiment, the composition may be incorporated in an article of confectionery, for example a sweet (i.e., chocolate), or a sweetened beverage.

Material S and Methods

Suitable materials and methods that were followed in the examples are now described.

Materials for the Cell Culture

RPMI 1640 medium, Dulbecco's Modified Eagles medium (DMEM), additives and fetal bovine serum (FBS) were from Gibco (Life Technologies, Basel, Switzerland). Bovine serum albumin (BSA) was purchased from Serologicals Proteins Inc. (Kankakee, Ill.).

Materials for Testing the Effect of CGMP

CGMP was obtained from R&D Konolfingen and was dissolved directly in Krebs Ringer Buffer. Two forms of CGMP, sodium extracted and calcium extracted, were tested as well as four fractions of CGMP.

Materials for Testing the Effect of Sweet and Acid Whey

For this study, conventional milk fractions at lab scale from fresh bovine milk from local markets were prepared.

Rennet (pressure simple) was obtained from Rhone Poulenc Roher, Cooperation Pharmaceutique Francaise, 77000 Melun France, Batch no. 1010089007, expiration date Sep. 21, 2000, 50 mg active chymosine per liter produced by TEXEL 38470 Vinay, France. $CaCl_2.2H_2O$, HCl 32%, acetic acid (glacial), and sodium hydroxide were also used.

Milk Fractions

Bovine Milk Fractions

Lab scale fractions were adapted from conventional milk processes. Centrifugation was realized at higher acceleration rates and non-soluble fractions were washed to increase selectivity and fraction efficacy.

Cream; Cream Washing and Skimmed Milk

Usually cream was extracted from whole milk by centrifugation between 3,000 and 4,500 g, and the selectivity of this step was improved by increasing acceleration u[ to 13,600 g using the fixed angle rotor SORVAL GS3 at 9,000 RPM for 30 minutes. Starting from 2,200 ml of whole milk, 90 g of cream were recovered as a top layer.

Cream washing (3 times labeled respectively, cream 1, 2 and 3): the cream layer was dispersed in 3 water volumes (270 ml) and gently scattered in a bottle by manual shaking before subsequent centrifugation.

Butter particles were spontaneously formed at the top of the bottle after the third cream washing and the buttermilk was recovered by sticking butter particles together.

A non-soluble fraction was recovered after centrifugation on the bottom of the bottles used for cream washings (Labelled: washed cream sediments).

Sweet Whey, Rennet Casein Washing and Rennet Casein

The separation of whey/casein is obtained by enzymatic treatment of skimmed milk inducing casein clotting. 520 µl of $CaCl_2$ 200 mM were added to 520 g of skimmed milk to reach 2 mM final concentration added. The skimmed milk was heated at 35° C. then 250 µl of rennet were immediately added with moderate magnetic stirring. After 1 min the blend was incubated 50 min at 35° C. in a water bath, poured into bottles for subsequent centrifugation (13,600 g for 30 min) to separate sweet whey from the non-soluble rennet casein.

Then, 476 g. of supernatant were fractionated in 10×1.3 aliquots (ependorf) and 40 ml plastic tubes. The material, labelled (Sweet whey), was frozen by immersion in liquid nitrogen and stored in a plastic bag at −20° C.

The rennet casein (45 g) was dispersed in 286 ml $CaCl_2$ 2 mM NaCl 0.9% and centrifuged, with the supernatant aliquoted, labeled (rennet casein washing) and then frozen in liquid nitrogen.

The 31 g of recovered rennet casein were dispersed in $CaCl_2$ 2 mM NaCl 0.9%, the volume was adjusted to 250 ml, and then was aliquoted, labeled (rennet casein) and frozen.

Acid Whey, Acid Casein Washing and Acid Casein

The separation of whey/casein is obtained by chemical acidification of skimmed milk inducing casein clotting. 520 µl of $CaCl_2$ 200 mM were added to 520 g of skimmed milk to reach 2 mM final concentration added. The skimmed milk was acidified at 25° C. by the addition of 32% HCl from pH 6.6 to pH 4.6 with moderate magnetic stirring. After 1 min of stirring, the blend was incubated 60 min at 25° C., poured into bottles for subsequent centrifugation (13,600 g for 30 min) to separate acid whey from the non-soluble acid casein.

Then, 503 g. of supernatant were fractionated in 10×1.3 aliquots (ependorf) and 40 ml plastic tubes. The material, labelled (Acid whey), was frozen by immersion in liquid nitrogen and stored in a plastic bag at −20° C.

The acid casein (41 g) was dispersed in 233 ml sodium acetate, pH 4.6, and centrifuged, with the supernatant (250 ml) aliquoted, labeled (Acid casein washing) and then frozen in liquid nitrogen.

The 28.6 g of recovered acid casein were dispersed in water, the pH was adjusted from 4.67 to 6.6 by NaOH addition and the volume was adjusted to 250 ml, and then was aliquoted, labeled (Acid casein) and frozen.

Cell Line and Culture Conditions

The human NCI-H716 cells, originally developed from a poorly differentiated caecal adenocarcinoma, were obtained from the American Type Culture Collection (ATCC, Rockville, Md., USA). Cells were grown in suspension at 37° C., 5% $CO_2$. The culture medium consisted of RPMI 1640 supplemented with 10% FBS, 2 mM L-glutamine, 100 IU/ml penicillin and 100 µg/ml streptomycin. Endocrine differentiation is enhanced in vitro in NCI-H716 cells grown on an extracellular matrix (de Bruine et al, 1993). Cells were, therefore, seeded in dishes coated with MATRIGEL® (Becton Dickinson, Bedford, Mass., USA) two days before experiments.

Secretion Studies

Two days before experiments, $1 \times 10^6$ cells were seeded in 12 well culture plates coated with MATRIGEL®. On the day of the experiment, the supernatant was replaced by Krebs-Ringer Bicarbonate Buffer (KRB) containing 0.2% wt/vol BSA with or without CGMP. Cells were incubated for 2 h at 37° C. Supernatants were collected with the addition of 50 µg/ml PMSF and frozen at −80° C. for subsequent analysis by radioimmunoassay (RIA) of GLP-1. Cells were scraped with a rubber policeman and homogenization buffer [1 N HCl containing 5% (v/v) HCOOH, 1% (v/v) trifluoroacetic acid (TFA), and 1% (v/v) NaCl] and sonicated for 15 s. Peptides were extracted from the cell medium and cell homogenates using an alcohol extraction as described by the supplier of the GLP-1 (7-36) Total RIA Kit (Linco Research Inc., St. Charles, Mo., USA). Concentrations of GLP-1 (Total, i.e., 7-36 amide or 9-36 amide) were measured using a commercial RIA kit (Linco Research Inc., St. Charles, Mo., USA). This kit measures GLP-1(7-36)$NH_2$ and GLP-1(9-36)NH2 with less than 0.4% crossreactivity with GLP-1(7-37). The $ED_{50}$ for the assay was 72 pM. The intraassay coefficient of variance was 2.28%.

Results

CGMP Stimulates the Release of GLP-1 in the NCI-H716 Intestinal Cell Line

The amount of GLP-1 released into the medium of NCI-H716 cells treated for 2 h with increasing concentrations (0.25-2.5 mg/ml wt/vol) of the calcium form of CGMP is shown in FIG. 1. Secretion of GLP-1 by NCI-H716 cells into the medium was normalized to the total GLP-1 content (secretion+cells) of the culture well and is expressed as a percentage of the control value. CGMP induced a dose-dependent increase in GLP-1 concentrations with maximum secretion reaching 259±77% (n=minimum of 3) of the control values with 2.5 mg/ml of CGMP-Ca. The symbol * represents a significant difference from control values ($p<0.05$).

Figure 2:
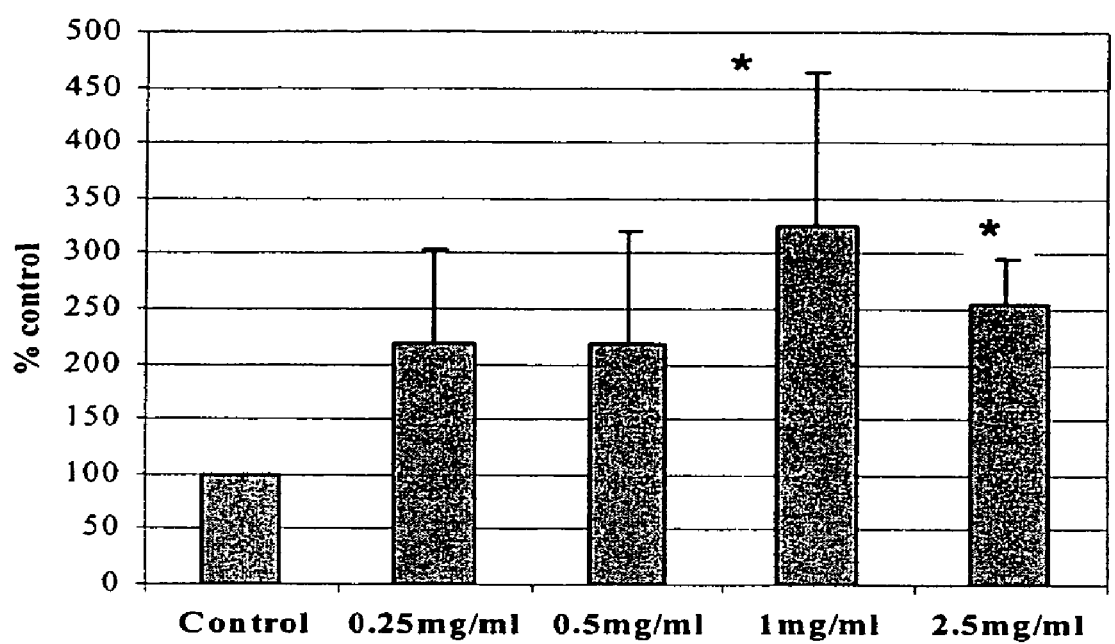
FIG. 2 shows secretion of GLP-1 by NCI-H716 cells in response to incubation for 2 h with different doses of CGMP-Na form.

FIG. 2 shows the amount of GLP-1 released into the medium of NCI-H716 cells treated for 2 h with increasing concentrations (0.25-2.5 mg/ml wt/vol) of the sodium form of CGMP. Again, secretion into the medium was normalized to the total cell content of the culture well and is expressed as a percentage of the control value. CGMP induced an increase in GLP-1 concentrations with maximum secretion reaching 255±41% (n=minimum of 3) of the control values with 2.5 mg/ml of CGMP-Ca. The symbol * represents a significant difference from control values ($p<0.05$).

Figure 3:
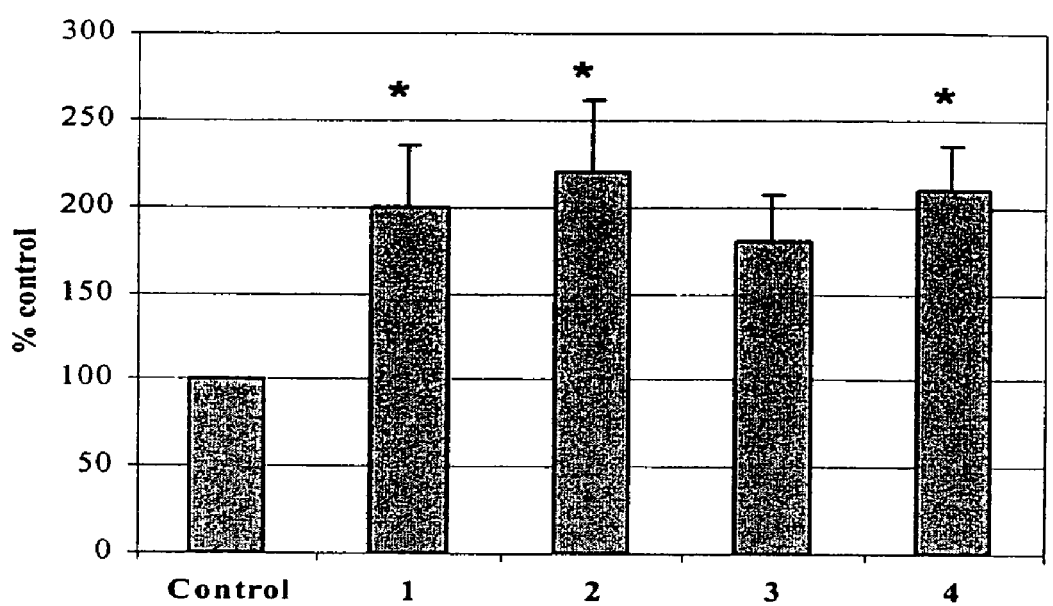
FIG. 3 shows secretion of GLP-1 by NCI-H716 cells in response to incubation for 2 h with different fractions of CGMP.

FIG. 3 shows secretion of GLP-1 by NCI-H716 cells in response to incubation for 2 h with different fractions of CGMP. Secretion into the medium was normalized to the total cell content of the culture well and is expressed as a percentage of the control value. The composition of the different fractions was the following:

Fraction 1) Hydrolyzed CGMP, pure peptidic material, no phosphorus, no sialic acid.

Fraction 2) Hydrolyzed CGMP, high sialic acid, high phosphorus content. Sample is in the Na-form.

Fraction 3) CGMP fraction enriched in CMPa and CMPb, the phosphorylated compounds of CGMP. Sample is in the Na-form.

Fraction 4) CGMP fraction enriched in sialic acid. Sample is in the Ca-form.

FIG. 3 shows that the amount of GLP-1 released into the medium by all fractions, except fraction 3 (p=0.085), was significantly increased with Fraction 2 resulting in the highest stimulation of 220±41% (n=3) of the control values. The symbol * represents a significant difference from control values (p<0.05).

Figure 4:
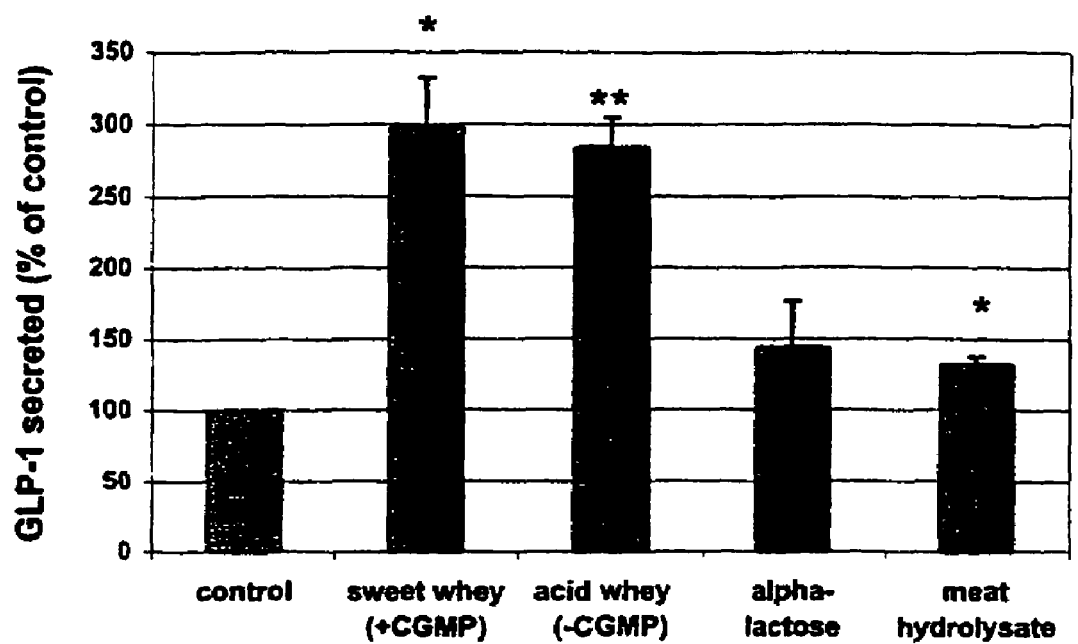
FIG. 4 shows secretion of GLP-1 by NCI-H716 cells in response to incubation for 2 h with sweet whey, acid whey and meat protein hydrolysates, as well as with an alpha-lactose dose to measure what effect the latter may have on the results.

Sweet and Acid Whey Stimulate the Release of Active GLP-1 in the NCI-H716 Intestinal Cell Line The amount of GLP-1 released into the medium after a 2 h incubation period in the presence of 5 mg/ml milk protein hydrolysates is shown in FIG. 4. Sweet whey and acid whey induced an increase in GLP-1 release of 298±34% and 284±21%, respectively, compared to the control (p=0.03 and 0.01, respectively, n=3). This effect was not due to the alpha-lactose content of these fractions, as the use of an equivalent alpha-lactose dose as the one contained in the different wheys only resulted in a small increase in GLP-1 secretion (144±32% compared to the control). Moreover, another protein hydrolysate, meat hydrolysate, did not induce such an effect on GLP-1 production when used in the same amount of 5 mg/ml (132±6% compared to the control).

The GLP-1 that was secreted and reported in FIG. 4 was measured differently that that of FIGS. 1-3. Here, a kit was used that only measures the active form of GLP-1, i.e., GLP-1 (7-37) or GLP-1 (7-36 amide), but not the degraded form, GLP-1 (9-36 amide), as was included in the data for FIGS. 1-3.

EXAMPLES

The following examples are given by way of illustration only and in no way should be construed as limiting the subject matter of the present application. Percentages and parts are by weight unless otherwise indicated.

Example 1

Preparation of CGMP

Bovine sweet whey was concentrated to 17% dry matter, demineralized by electrodialysis, freed of cations on a strong cationic resin column, freed of anions on a weak anionic resin column and spray-dried in a drying tower. An analysis of the components of this composition is provided in the following table:

| Component | Percentage present |
|---|---|
| Proteins (GMP included) | 11.7 |
| Lactose | 81.7 |
| Ash | 1 |
| Lipids | 1 |
| Water | balance to 100 |

The demineralized whey powder was solubilized in deionized water. After cation removal, the solution has an initial pH of 3.8. In the preceding plant, 392 kg of this solution was treated at the temperature of 8° C., while stirring it in the reactor in the presence of 23 kg of weak anionic resin of hydrophobic matrix based on polystyrene (IMAC HP 661®, Rohm & Haas, regenerated in OH— form) for 4 h. Stabilization of the pH at 4.89 indicates the end of the reaction. The liquid was drawn off and the resin was recovered as above.

After concentration of the liquid to 45% dry matter by evaporation, the concentrate was spray-dried in a drying tower.

Analysis of the concentrate by HPLC showed that the reaction removed 89% of the starting CGMP. Moreover, the powder contained 9.1% of whey protein, which corresponded to a yield of 90% of the whey proteins.

To recover CGMP, the resin was washed successively with deionized water, with 30 l of an aqueous solution at 0.5% HCl and with 30 l of deionized water, and the CGMP was eluted twice with 40 l of aqueous solution at 2% Ca(OH)$_2$. Rinsing is carried out with 30 l of deionized water. After combining the eluate and rinsing volumes, the combination was concentrated to a volume of 25 l by ultrafiltration with a membrane having a nominal cut-off of 3000 daltons. The retentate was freeze-dried and 900 g of CGMP were obtained, corresponding to a yield of 80% relative to the starting CGMP.

Example 2

Fermented Milk Containing CGMP or Whey Powder

A traditional fermented milk containing 1-4% fats was prepared as follows: After standardizing whole milk, low fat milk or a mixture of both, 0.05% by weight of CGMP as prepared in Example 1 is added. The mixture was then pasteurized in a plate exchanger, the liquid was cooled to the fermentation temperature, a thermophilic or mesophilic lactic ferment was added and incubation was carried out until a pH of <5 was obtained.

Subsequent filling and sealing pots took place in a conventional manner.

Alternative embodiments having additions of 0.1%, 0.25% and 0.5% by weight of CGMPs and commercial whey powder have been prepared.

Example 3

Fermented and Gelled Milk Enriched in Probiotic Bacteria Containing CGMP or Whey Powder Fermented and gelled milks were prepared enriched in probiotic bacteria. 89.3 parts milk containing fat were mixed with 3.7 parts of skimmed milk powder and about 0.05 by weight of CGMP as prepared in Example 1, then the mixture was preheated to 70° C. and pasteurized at 92° C./6 min, and after having been cooled to 43° C. the mixture was inoculated with 2% of a common yogurt starter comprising Streptococcus thermophilus and Lactobacillus bulgaricus and with 5% of Lactobacillus johnsonii (La-1, CNCM I-1225). After conditioning in pots, fermentation was carried out at 38° C. up to pH 4.6 and the pots were then cooled to 6° C.

The following amounts of CGMP or commercial whey powder were added: 0.1%, 0.25% and 0.5% by weight.

Example 4

Fermented and Gelled Milk Enriched in Probiotic Bacteria Containing CGMP or Whey Powder Fermented and gelled milks are prepared as described in the previous example, wherein Lactobacillus johnsonii strain is replaced by Lactobacillus acidophilus La-10 (Nestle Culture collection, Lausanne, Switzerland) (ATCC 11975).

Example 5

Enteral Composition Containing CGMP

An enteral composition with an energy density of 6.3 kJ/ml and 8% (p/v) of proteins was prepared from "low temperature" skimmed milk powder, i.e. skimmed milk dried under controlled thermal conditions.

20 kg of low temperature skimmed milk powder was dispersed in 100 kg of demineralized water at a temperature of about 50-55° C. This dispersion is microfiltered by passing demineralized water through until 600 kg of permeate have been eliminated. The retentate is then further concentrated to around 60 kg, which represents a dry matter content of 21% with a protein content, based on dry matter, of 82%.

To prepare the enteral composition, 2.3 kg of liquid retentate are mixed at 55° C. with 600 g of maltodextrin, 200 g of sucrose, 20.3 g of Tri-K citrate $H_2O$, 9.2 g of $MgCl_2 6H_2O$, 5.8 g of NaCl and about 0.5 to 1% by weight of CGMP as prepared in Example 1.

After the ingredients were dissolved in the retentate, demineralized water is added to a total weight of the dispersion of 4.7 kg. The pH was adjusted to 6.8, after which 300 g of fatty phase are introduced, the total weight of the dispersion being 5 kg.

After homogenization and sterilization, the product had an agreeable sugary taste.

Example 6

Cereal Bar Containing CGMP

In order to prepare an expanded starting product, barley, wheat, corn or oat flour was treated in a twin-screw extruder for about 15 seconds at a screw speed of about 350 RPM. in the presence of approximately 12% of water. After this treatment, the expanded product left the extruder in the form of 2 to 3 mm long granules that were dried for 20 minutes at 100° C.

The product thus obtained had a cellular structure and has the following composition:

| | |
|---|---|
| Edible fibers | 31% |
| Proteins | 21% |
| Glucides | 37.5% |
| Lipids | 6.5% |
| Ash | 2.4% |
| Water | 1.6% |

The expanded product was incorporated in a bar intended for treatment of diabetes, which had the following composition:

| | |
|---|---|
| Expanded product | 39.4% |
| Oat flakes | 16.7% |
| Sorbitol | 8.4% |
| Fructose | 8.5% |
| Apple cubes | 6.1% |
| Rice crispies | 4.1% |
| Gelatin | 4.0% |
| Apricot powder | 2.5% |
| Palm oil | 3.0% |
| CGMP as prepared in example 1 | 2.5% |
| Water | 4.8% |

Example 7

Food Supplement Containing CGMP

A culture of the strain Lactobacillus johnsonii La-1 (CNCM I-1225) of human origin, was mixed with CGMP as prepared in example 1 and spray dried according to the process given in EP0818529 so as to obtain a food supplement containing an amount of about 5% by weight of CGMP.

The powder obtained may be used as a food supplement. A breakfast cereal, milk product or another food product may then be sprinkled with this powder containing CGMP.

Example 8

Food Supplement Containing CGMP

A food supplement was prepared as described in example 9. However, Lactobacillus johnsonii was replaced by Lactobacillus acidophilus, La-10 (Nestec collection, Lausanne, Switzerland) or a mixture of the two strains.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

The invention is claimed as follows:

1. A method for assessing proglucagon gene expression and GLP-1 release by human cells which comprises:
   obtaining a cell line derived from an adenocarcinoma of human caecum, wherein the cell line is a NCI-H716 cell line having the ATCC number CCL-251;
   treating the cell line with a composition comprising a milk protein hydrolysate; and
   measuring the amount of GLP-1 secreted by the cell line.

2. The method of claim 1, wherein the milk protein hydrolysate is selected from the group consisting of whey, a form of CGMP, and combinations thereof.

* * * * *